United States Patent
Shi et al.

(10) Patent No.: US 10,732,101 B1
(45) Date of Patent: Aug. 4, 2020

(54) NON-DESTRUCTIVE GAS CONCENTRATION ANALYZER

(71) Applicant: Enos Analytical, LLC, Acton, MA (US)

(72) Inventors: Quan Shi, West Roxbury, MA (US); Allan S. Tseng, Chelmsford, MA (US)

( * ) Notice: Subject to any disclaimer, the term of this patent is extended or adjusted under 35 U.S.C. 154(b) by 0 days.

(21) Appl. No.: 16/248,469

(22) Filed: Jan. 15, 2019

(51) Int. Cl.
  *G01N 21/35* (2014.01)
  *G01K 13/00* (2006.01)
  *G01N 21/3504* (2014.01)
  *G01N 21/359* (2014.01)

(52) U.S. Cl.
  CPC ......... *G01N 21/3504* (2013.01); *G01K 13/00* (2013.01); *G01N 21/359* (2013.01); *G01N 2021/3513* (2013.01)

(58) Field of Classification Search
  CPC .. G01K 13/00; G01N 21/3504; G01N 21/359; G01N 2021/3513
  See application file for complete search history.

(56) References Cited

U.S. PATENT DOCUMENTS

| | | | |
|---|---|---|---|
| 3,509,996 | A | 5/1970 | Malik |
| 5,473,161 | A | 12/1995 | Nix et al. |
| 5,614,718 | A | 3/1997 | Brace |
| 9,546,916 | B1 * | 1/2017 | Crane ................... B65D 79/02 |
| 2005/0084974 | A1 | 4/2005 | Veale et al. |
| 2006/0181410 | A1 * | 8/2006 | Staples ................... G01K 1/14 340/539.1 |
| 2017/0299455 | A1 | 10/2017 | Forestelli et al. |

FOREIGN PATENT DOCUMENTS

| | | |
|---|---|---|
| CN | 203414177 U | 1/2014 |
| EP | 2372344 B1 | 10/2011 |
| JP | 2009014589 A | 1/2009 |

(Continued)

OTHER PUBLICATIONS

FMS—Carbon Dioxide CO2 Headspace Analysis, webpage [Online]. Lighthouse Instruments, 2018 [retrieved on Oct. 16, 2018]. Retrieved from the Internet: <URL: www.lighthouseinstruments.com/fms-carbon-dioxide-co2-headspace-analysis>.

(Continued)

*Primary Examiner* — Mark R Gaworecki
(74) *Attorney, Agent, or Firm* — Verrill; John W. Powell

(57) ABSTRACT

A gas analyzer to non-destructively detect the concentration of a gas in a container includes a sensor unit with an infrared emitter configured to transmit infrared radiation over a path through the container. There is an infrared detector configured to receive a portion of the infrared radiation transmitted by the infrared emitter and to produce an output signal corresponding to the received radiation. There is a processor module, in communication with the sensor unit, configured to receive the detected spectrum from the infrared detector, the detected spectrum including a trough region at wavelengths which absorb the gas in the pressurized container. The processor is also configured to form an interpolated baseline spectrum from the detected spectrum by interpolating baseline data points spanning the trough region and to calculate a gas concentration in the container using the detected spectrum and the interpolated baseline spectrum.

34 Claims, 7 Drawing Sheets

(56) References Cited

FOREIGN PATENT DOCUMENTS

| JP | 2016 024000 A | 2/2016 |
|---|---|---|
| WO | 2017/182964 A1 | 10/2017 |

OTHER PUBLICATIONS

OST—Optical Shelf-Life Tester, webpages [Online]. Steinfurth Electromechanical Measuring Systems, 2018 [retrieved on Oct. 17, 2018]. Retrieved from the Internet: <URL: https://www.steinfurth.com/page,co2-measuring-instruments,steinfurth-ost-optical-shelf-life-tester,0,0,12,0,en.htm>.

OST—Optical Shelf-Life Tester Incl. Teach Head, Datasheet [Online]. Steinfurth Electromechanical Measuring Systems, 2018 [retrieved on Oct. 17, 2018]. Retrieved from the Internet: <URL: https://www.steinfurth.com/page,co2-measuring-instruments,steinfurth-ost-optical-shelf-life-tester,0,0,12,0,en.htm>.

Partial International Search Report and Provisional Opinion dated Apr. 14, 2020, received in international patent application No. PCT/US20/013610, 11 pages.

Khair Zineb Miftah et al: "In situ measurements of methane in the troposphere and the stratosphere by the Ultra Light SpEctrometer Amulse", Applied Physics B: Lasers and Optics, Springer International, Berlin, DE, vol. 123, No. 12, Nov. 13, 2017, (Nov. 13, 2017), pp. 1-11, XP036377651, ISSN: 0946-2171, DOI: 10.1007/S00340-017-6850-4 [retrieved on Nov. 13, 2017].

Deng Hao et al: "Quantum cascade laser based sensor for open path measurement of atmospheric trace gases", Proceedings of SPIE; [Proceedings of SPIE ISSN 0277-786X vol. 10524], SPIE, US, vol. 10250, Feb. 10, 2017, pp. 1025020-1025020.

Yedhu Krishna et al: "Baseline correction for stray light in log-ratio diode laser absorption measurements", Applied Optics, Optical Society of America, Washington, DC, US, vol. 53, No. 19, Jul. 1, 2014 (Jul. 1, 2014), pp. 4128-4135, XP001590892, ISSN: 0003-6935, DOI:10.1364/A0.53.004128 [retrieved on Jun. 23, 2014].

Ghysels M et al: "Temperature dependences of air-broadening, air-narrowing and line-mixing coefficients of the methane [nu]3R(6) manifold lines-Application toin-situmeasurements of atmospheric", Journal of Quantitative Spectroscopy and Radiative Transfer, Elsevier Science, Oxford, GB, vol. 133, Aug. 13, 2013 (Aug. 13, 2013), pp. 206-216, XP028779435, ISSN: 0022-4073.

Joly L. et al: "Development of a spectrometer using a continuous wave distributed feedback quantum cascade laser operating at room temperature for the simultaneous analysis of N20 anc CH4 in the Earth's atmosphere", Applied Optics, Optical Society of America, Washington,DC, US, vol. 47, No. 9, Mar. 20, 2008 (Mar. 20, 2008), pp. 1206-1214, XP001512974, ISSN: 0003-6935.

Yu Lin et al: "Development of an intra-cavity gas detection system based on L-band erbium-doped fiber ring laser", Sensors and Actuators B: Chemical, Elsevier BV, NL, vol. 193, Dec. 11, 2013 (Dec. 11, 2013), pp. 356-362, XP028818799, ISSN: 0925-4005.

International Search Report and Written Opinion dated Jun. 6, 2020, received in international patent application No. PCT/US2020/013610, 26 pages.

\* cited by examiner

NON-DESTRUCTIVE GAS CONCENTRATION ANALYZER

FIELD OF THE INVENTION

This invention relates to a non-destructive gas concentration analyzer and more specifically to a non-destructive gas concentration analyzer which may more rapidly determine gas concentration in a variety of transparent or semi-transparent containers filled with a solution sealed under pressure.

BACKGROUND OF THE INVENTION

Plastic materials are often used as containers for beverages and, for carbonated beverages, the plastic material forms a barrier against permeation of the gas, e.g. carbon dioxide, which provides the carbonation. A reduction of the carbon dioxide permeation rate helps to maintain a high level of carbonation in the carbonated beverages. Therefore, the choice of suitable plastic material, the distribution of the material, and the processing conditions are important factors in producing such plastic containers. One major difficulty with volume production of plastic containers is that periodic sampling of production containers is required to ensure that the container is performing to the desired specifications and containing carbon dioxide as desired.

Originally, the periodic sampling of plastic containers required actual, direct measurement of the carbon dioxide in the container. This was complex and required large test equipment, including plumbing and precision gas detectors, to destructively test the plastic containers. In addition, since the decrease over time in carbonation level in a sealed container may be slight, a test cycle would usually last for several weeks before an estimate of carbonation loss rate could be obtained for predicting the shelf life of a carbonated beverage.

Non-destructive carbon dioxide testing systems, which allow for more rapid testing of plastic containers during production, have been developed. One such system is described in U.S. Pat. No. 5,614,718, which requires the creation of a prediction model using one or more analysis containers. The analysis containers are subjected to spectral analysis using near infrared (NIR) transmission to acquire spectral signatures from the one or more containers. The containers are also physically measured to obtain the dimensions which are then stored as calibration data. From the spectral analysis and the calibration data, prediction models are created and then used to non-invasively test production containers filled with carbonated beverages to predict carbonation retention and shelf-life. The non-invasive testing of production containers involves transmitting NIR energy through the production container and measuring the received NIR energy. Using the received energy and the prediction model, carbonation retention may be determined.

This non-destructive test system reduces carbon dioxide retention test times from several weeks, as described above with the destructive testing, to minutes or less. However, a new prediction model is required for each new container type to be tested. Moreover, this system is suitable for use in a carbonated beverage facility and not for field testing carbonation levels of carbonated beverages on the shelf in stores or in inventory.

Therefore, there is a need for a smaller and simpler non-destructive carbonation concentration analyzer which may more rapidly test for carbon dioxide concentration in the field in a variety of transparent or semi-transparent containers without the need for predetermined prediction models, such as described in U.S. Pat. No. 5,614,718.

BRIEF SUMMARY OF THE INVENTION

The benefits and advantages of the present invention over existing systems will be readily apparent from the Brief Summary of the Invention and Detailed Description to follow. One skilled in the art will appreciate that the present teachings can be practiced with embodiments other than those summarized or disclosed below.

In one aspect the invention features a gas analyzer to non-destructively determine the concentration of a gas in a pressurized transparent or semitransparent container having a neck portion extending from a shoulder and terminating in an opening, the opening being sealed with a cap. There is a sensor unit including a first surface, a second surface, opposite the first surface, and a sensor region between the first and second surfaces. The sensor region includes a first end having a stop surface and the second end including an aperture, in communication with the sensor region, configured to receive a neck portion of a container in the sensor region until a cap contacts the stop surface. The sensor unit further includes at least one sidewall extending from the first surface toward the second surface and an infrared emitter affixed to the at least one sidewall and configured to transmit infrared radiation across the sensor region. There is an infrared detector affixed to the at least one sidewall, opposite the infrared emitter, and configured to receive infrared radiation transmitted by the infrared emitter across the sensor region and to provide an output signal corresponding to the received infrared radiation. The infrared emitter and the infrared detector are each affixed to the at least one sidewall, spaced a distance, d, from the stop surface in the direction of the aperture, wherein the distance, d, corresponds to a predetermined distance from the cap to a location on the neck portion of the container. There is a processor module, in communication with the sensor unit, configured to receive the output signal from the infrared detector and to determine a concentration of the gas in the container.

In other aspects of the invention one or more of the following features may be included. The infrared radiation may comprise near infrared radiation. The sensor unit may include four sidewalls, and the infrared transmitted may be affixed to a first sidewall and the infrared detector is affixed to a second sidewall opposite the first sidewall. Spacing the infrared transmitter and the infrared detector the distance, d, from the stop surface in the direction of the aperture, which corresponds to a predetermined distance from the cap to a location on the neck portion of the container, may provide a fixed transmission path length across the neck portion of the container. The processor module may be separate from the sensor unit and it may include a display device configured to display the concentration of the gas determined to be in the container. The container may be partially filled with a liquid and the interior region of the container above the liquid constitutes a headspace, and the distance d from the cap to a location on the neck portion of the container may be positioned within the headspace. There may also be included a temperature sensor in communication with the sensor region and the processor module may use the output signal to determine a gas concentration in the headspace, and from the gas concentration in the head space and a temperature measured in the sensor region by the temperature sensor, the processor module may determine a gas concentration in the liquid.

In another aspect, the invention features a gas analyzer to non-destructively detect the concentration of a gas in a pressurized transparent or semi-transparent container. There is a sensor unit including an infrared emitter configured to be positioned on a first side of a pressurized container and to transmit infrared radiation over a path through the pressurized container. The infrared radiation has an infrared spectrum including wavelengths which absorb a gas in the pressurized container and wavelengths which do not absorb the gas in the pressurized container. There is an infrared detector configured to be positioned on a second side of the pressurized container, opposite the first side, and configured to receive a portion of the infrared radiation transmitted by the infrared emitter over the path through the pressurized container and to produce detected spectrum corresponding to the received radiation. There is also a processor module, in communication with the sensor unit, configured to receive the detected spectrum from infrared detector. The detected spectrum includes a trough region at wavelengths which absorb the gas in the pressurized container. The processor is also configured to form an interpolated baseline spectrum from the detected spectrum by interpolating baseline data points spanning the trough region and it is configured to calculate a gas concentration in the pressurized container using the detected spectrum and the interpolated baseline spectrum.

In further aspects of the invention one or more of the following features may be included. The infrared radiation may comprise near infrared radiation. The sensor unit may include a first surface, a second surface, opposite the first surface, and a sensor region between the first and second surfaces. The sensor region may be within the sensor unit and include a first end having a stop surface and the second end may include an aperture, in communication with the sensor region. The aperture may be configured to receive a neck portion of a container in the sensor region until a cap contacts the stop surface. The sensor unit may further include at least one sidewall extending from the first surface toward the second surface. The sensor unit may include four sidewalls, and the infrared transmitted may be affixed to a first sidewall and the infrared detector may be affixed to a second sidewall opposite the first sidewall. The infrared emitter and the infrared detector may each be affixed to the at least one sidewall, spaced a distance, d, from the stop surface in the direction of the aperture, wherein the distance, d, corresponds to a predetermined distance from the cap to a location on the neck portion of the container. Spacing the infrared transmitter and the infrared detector the distance, d, from the stop surface in the direction of the aperture, which corresponds to a predetermined distance from the cap to a location on the neck portion of the container, may provide a fixed transmission path length across the neck portion of the container.

In yet further aspects of the invention one or more of the following features may be included. The processor module may be separate from the sensor unit and it may include a display device configured to display the concentration of the gas determined to be in the container. The container may be partially filled with a liquid and the interior region of the container above the liquid constitutes a headspace, and the distance d from the cap to a location on the neck portion of the container may be positioned within the headspace. There may further be a temperature sensor in communication with the sensor region and the processor module may use the output signal to determine a gas concentration in the headspace. From the gas concentration in the head space and a temperature measured in the sensor region by the temperature sensor, the processor module may determine a gas concentration in the liquid. The processor module may further be configured to use a plurality of data points on each side of the trough to perform a non-linear curve fitting to obtain the baseline data points spanning the trough region. The processor module may further be configured to divide the detected spectrum by the interpolated baseline spectrum to produce a normalized spectrum indicative of the energy received by infrared detector. The processor module may also be configured to determine an absorbance of energy due to the gas using the normalized spectrum and, using the absorbance of energy, calculate a concentration of the gas in the headspace of the container. The processor module may be configured to, using the concentration of the gas in the headspace and the temperature in the sensor region, determine a concentration of the gas dissolved in the liquid.

In another aspect, the invention features a method to non-destructively detect the concentration of a gas in a pressurized transparent or semi-transparent container. The method includes transmitting, using an infrared emitter positioned on a first side of a pressurized container, infrared radiation over a path through the pressurized container. The infrared radiation has an infrared spectrum including wavelengths which absorb a gas in the pressurized container and wavelengths which do not absorb the gas in the pressurized container. The method also includes receiving, using an infrared detector positioned on a second side of the pressurized container, opposite the first side, a portion of the infrared radiation transmitted by the infrared emitter over the path through the pressurized container and to produce detected spectrum corresponding to the received radiation. The method additionally includes receiving the detected spectrum from infrared detector, the detected spectrum including a trough region at wavelengths which absorb the gas in the pressurized container and forming an interpolated baseline spectrum from the detected spectrum by interpolating baseline data points spanning the trough region. The method then involves calculating a gas concentration in the pressurized container using the detected spectrum and the interpolated baseline spectrum.

In further aspects of the invention one or more of the following features may be included. The infrared radiation may comprise near infrared radiation. The infrared transmitter and the infrared detector may be spaced a predetermined distance from a cap of the container to a location on the neck portion of the container to provide a fixed transmission path length across the neck portion of the container. The method may include including displaying the concentration of the gas determined to be in the container. The container may be partially filled with a liquid and the interior region of the container above the liquid constitutes a headspace, and the fixed transmission path length may be positioned within the headspace. The method may further include determining a temperature proximate the container, using the detected spectrum to determine a gas concentration in the headspace, and, from the gas concentration in the head space and temperature proximate the container, determining a gas concentration in the liquid. The method may additionally include using a plurality of data points on each side of the trough to perform a non-linear curve fitting to obtain the baseline data points spanning the trough region and dividing the detected spectrum by the interpolated baseline spectrum to produce a normalized spectrum indicative of the energy received by infrared detector. The method may also include determining an absorbance of energy due to the gas using the normalized spectrum and using the absorbance of energy, to calculate a concentration of the gas in the headspace of the container. The method may further include using the concentration of the gas in the headspace and the temperature in the sensor region, to determine a concentration of the gas dissolved in the liquid.

These and other features of the invention will be apparent from the following detailed description and the accompanying figures.

BRIEF DESCRIPTION OF THE FIGURES

Embodiments of the present invention will now be described, by way of example only, with reference to the attached Figures, wherein.

DETAILED DESCRIPTION OF INVENTION

Figure 1:
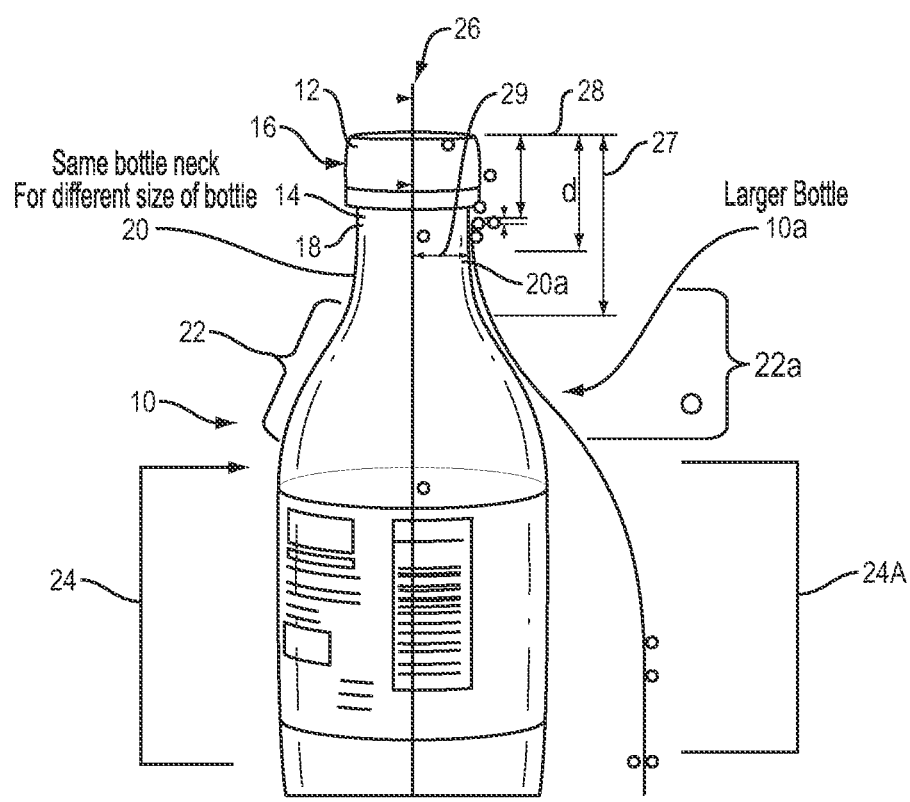
FIG. 1 is a cross-sectional view of an example beverage container the carbonation of which may be measured with the gas analyzer according to the invention.

The disclosure and the various features and advantageous details thereof are explained more fully with reference to the non-limiting embodiments and examples that are described and/or illustrated in the accompanying drawings and detailed in the following description. It should be noted that the features illustrated in the drawings are not necessarily drawn to scale, and features of one embodiment may be employed with other embodiments as the skilled artisan would recognize, even if not explicitly stated herein. Moreover, it is noted that like reference numerals represent similar parts throughout the several views of the drawings.

Descriptions of well-known components and processing techniques may be omitted so as to not unnecessarily obscure the embodiments of the disclosure. The examples used herein are intended merely to facilitate an understanding of ways in which the disclosure may be practiced and to further enable those of skill in the art to practice the embodiments of the disclosure. Accordingly, the examples and embodiments herein should not be construed as limiting the scope of the disclosure.

A preferred embodiment of this invention is described in the context of a non-destructive carbon dioxide analyzer for use with transparent or semi-transparent carbonated beverage bottles to detect carbon dioxide concentrations in such bottles. However, this invention is more broadly applicable to detecting concentrations of any gaseous specious in any type (plastic, glass, etc.) or shape of transparent or semi-transparent container.

Containers for carbonated beverages are typically formed of a plastic material, such as polyethylene terephthalate (PET), which may be produced using, for example, a blow molding process, such as injection stretch blow molding. In a two-stage injection stretch blow molding process, the plastic is first molded into a "preform" using the injection molding process. Preforms are produced with the necks of the bottles, including threads (the "finish") on one end. These preforms are fed (after cooling) into a reheat stretch blow molding machine to produce the desired bottle shape.

With the blow molding process, the bottle necks have standard dimensions, even with varying body shapes/sizes. The non-destructive carbon dioxide analyzer described herein takes advantage of the standard neck dimensions, as described below. It should be noted that any bottle/container may be used with the non-destructive carbon dioxide analyzer described herein, provided its neck dimensions are known.

Referring to FIG. 1, there is shown a typical plastic bottle 10 formed using the above described blow molding process. Bottle 10 includes sealing surface (not shown), which is a flat, circular top surface forming the opening of the bottle. The sealing surface makes direct contact with a closure/cap 12 to form a seal. Spiral threads on the bottle below the sealing surface mesh with threads on the inside of the closure/cap 12 to seal the bottle 10. The top part of bottle 10 from the sealing surface to the neck ring 14 is called the finish 16. There is a seam at the base of the neck ring 14 called the neck ring parting line 18, which marks the joining of the finish 16 to the neck 20 of the bottle. Transitioning from the neck 20, there is formed a shoulder 22, which increases in diameter until the shoulder meets the sidewall 24 of the bottle, which is the widest portion of the bottle.

In general, bottles that contain carbonated beverages are formed using a standard size finish and neck, as formed during the extrusion process, and the shoulder and body of the bottle, which are formed during the blowing process, may vary from bottle design to bottle design. By knowing standard dimensions of a particular carbonated bottle design, one will know the cross-sectional dimensions (i.e. the radius) of the bottle along the longitudinal axis 26 from the sealing surface to the base of the bottle. This is illustrated in FIG. 1, where the outline of a larger bottle 10a is shown. As depicted by the outline of bottle 10a, the finish 16, and neck 20 of both bottle 10 and bottle 10a are the same. Shoulder 22a of bottle 10a is larger than shoulder 22 of bottle 10 and sidewall 24a of bottle 10a is shown to have a much larger radius than sidewall 24 of bottle 10.

For this example of bottle designs, certain dimensions of the finish 16 and neck 20 are depicted in FIG. 1, which are the same for both bottles 10 and 10a. The distance from the top of cap 12 to the transition point from the neck 20/20a to the shoulder 22/22a is shown to be 38.34 mm, as indicated by line 27. The distance from the top of cap 12 to the top of neck ring 14 is shown to be 17.70 mm, as indicated by line 28, and the distance from the top of neck ring 14 to the neck ring parting line 18 is 1.37 mm. Thus, the total distance from the top of cap 12 to the neck ring parting line is 19.07 mm (17.70 mm+1.37 mm) and from there to the transition point between the neck 20/20a and the shoulder 22/22a is 19.27 mm (38.34 mm-19.07 mm). Between the neck ring parting line and the transition between the neck and the shoulder, the two bottles have the same cross-sectional dimensions. Thus, by selecting a point in this region the radius/diameter of the bottles will be known. For example, as indicated by radius line 29, which is a distance d from the top of cap 12, the radius/diameter is 13 mm/26 mm.

As will be described below, knowing the radius/diameter of one or more bottle designs, the path length of NIR energy transmitted through the bottle may be known and used to calculate gas concentration. According to an aspect of this invention, a spectrum of NIR energy may be transmitted across a bottle/container holding, among other things, one or more gaseous species, and the absorbance of energy at a desired wavelength, corresponding to the gaseous species, may be measured to determine the concentration of the gaseous species. The transmitted path will typically be across the headspace of the bottle/container, i.e. the portion of the bottle/container above the liquid. Therefore, the gas concentration in the headspace may first be determined and from that the gas concentration dissolved in the liquid may be determined.

While the primary application described herein is measuring the concentration of carbon dioxide in a carbonated beverage bottle, this invention is more generally applicable to the measurement of various gaseous species present in any transparent or semi-transparent container.

By selecting a particular point along the length of a bottle, having a known bottle design, to transmit a spectrum of NIR energy, the radius of the bottle will be known and thus the path length, l, of the radiation transmitted through the bottle will be known. The path length, l, is one of the variables in the Beer-Lambert Law equation, which may be expressed as follows:

$$A = \varepsilon l c \qquad \text{Equation (1)}$$

In this equation, A is the absorbance of energy, ε (epsilon) is the molar absorptivity or the molar absorption coefficient and c is the concentration of the gaseous species in the solution. With the path length, l, known, the molar absorption coefficient, ε, being a fixed value, and the absorbance A determinable, as set forth below, the concentration, C, may be calculated using a non-destructive gas concentration analyzer according to this invention.

Figure 2A:
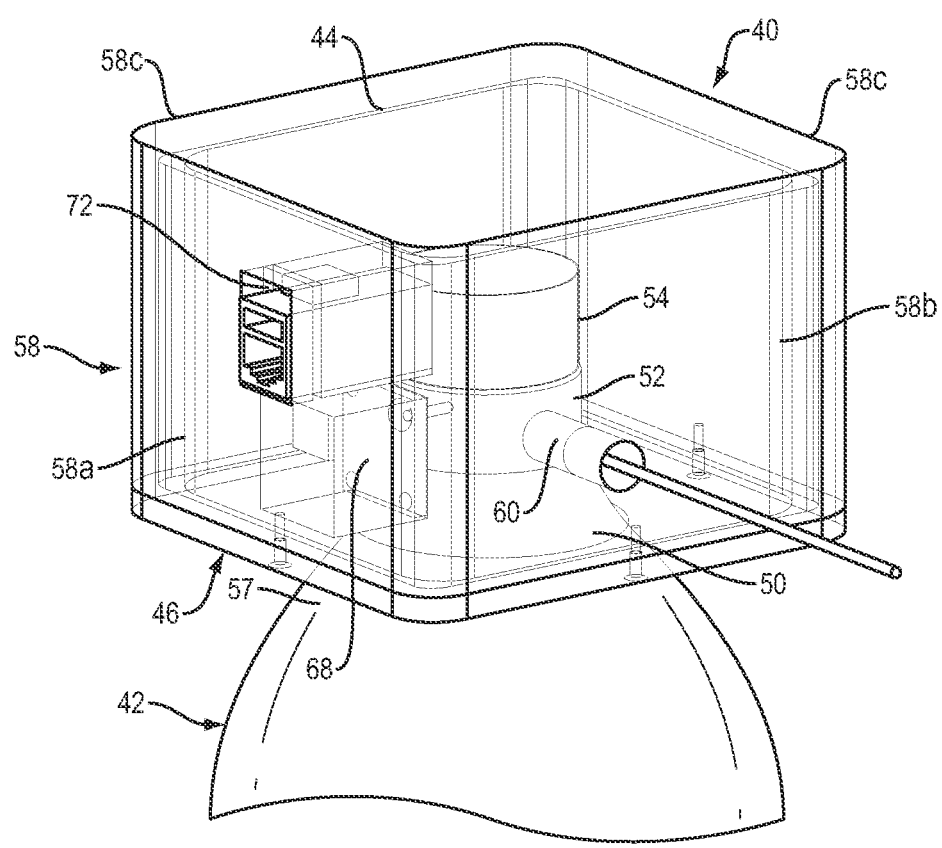
FIG. 2A is a perspective view of the sensor unit of the gas analyzer according to the invention.
Figure 2B:
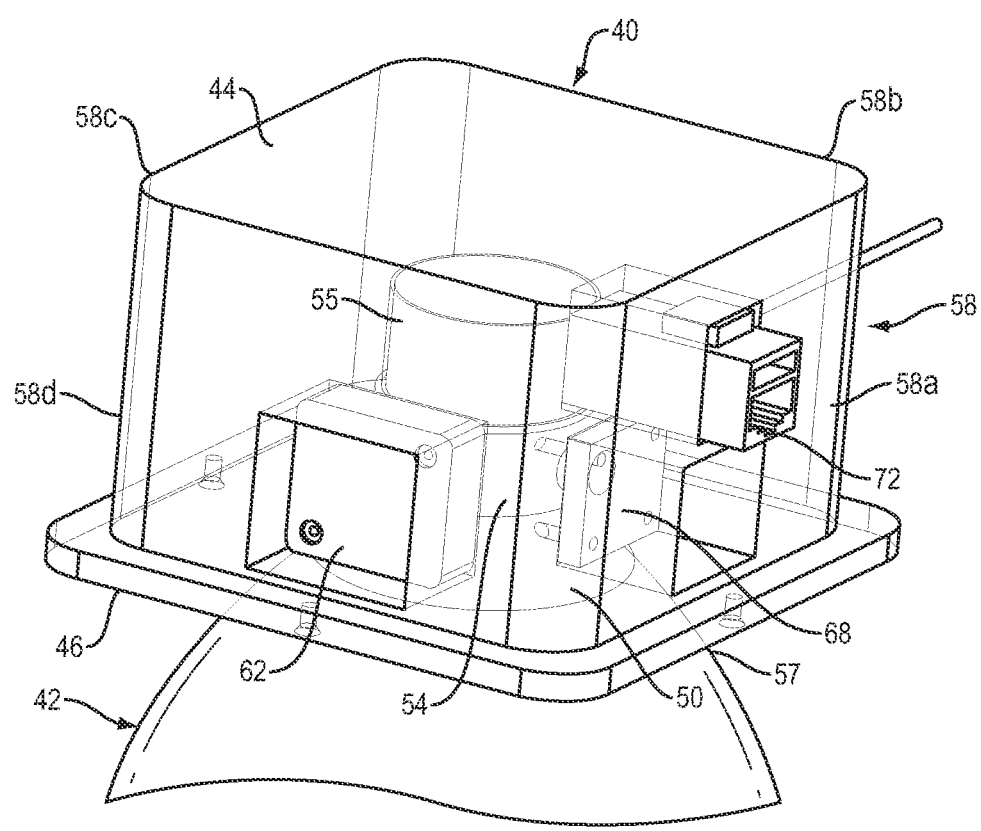
FIG. 2B is an alternative perspective view of the sensor unit depicted in FIG. 2A.
Figure 3:
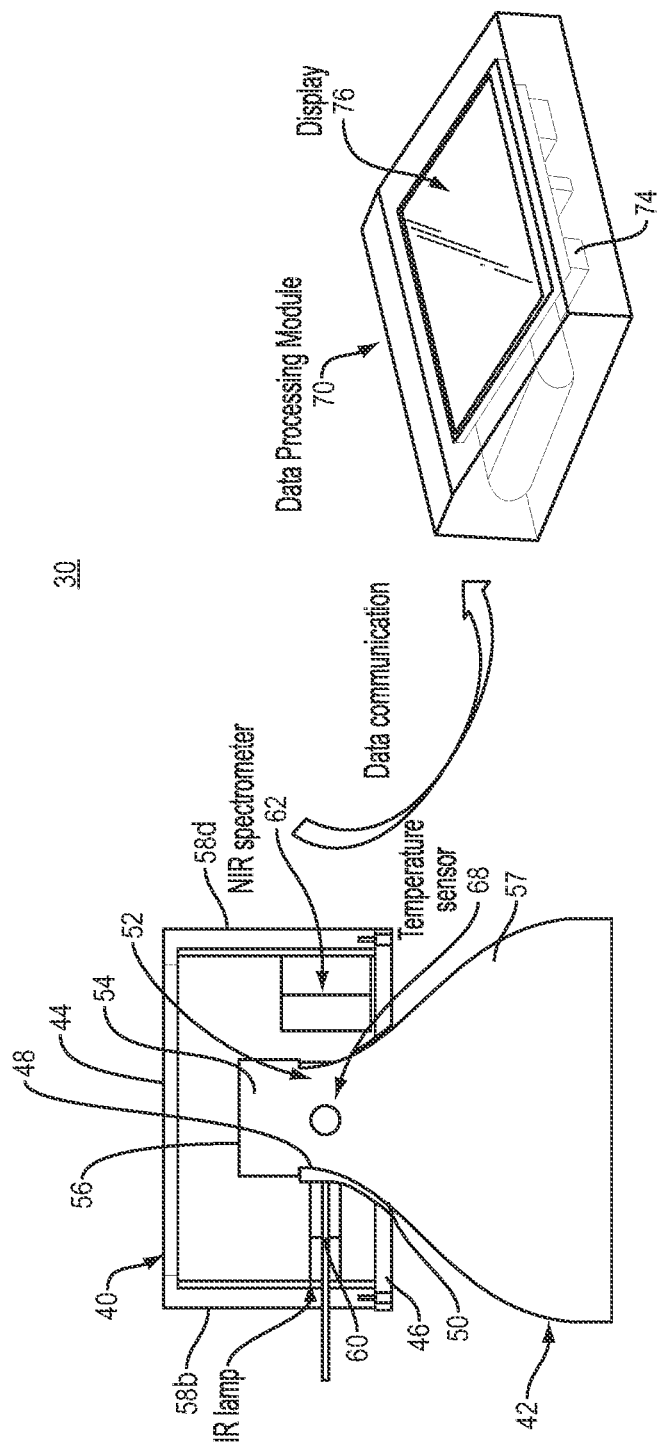
FIG. 3 is a cross-sectional view of the sensor unit depicted in FIG. 2A and a perspective view of the data processing of the gas analyzer according to the invention.

Referring to FIGS. 2A and 2B, perspective views, and FIG. 3, a cross-sectional view, of a sensor unit 40 of an embodiment of a non-destructive gas concentration analyzer 30 according to this invention is shown. The sensor unit is shown to be disposed on a plastic bottle 42 similar to the bottle depicted in FIG. 1. Bottle 42 is of a known design and contains a carbonated beverage. Sensor unit 40, which may be formed in a cube shape and be made of a plastic material, includes a top surface 44, a bottom surface 46, opposite the top surface 44, and a sensor region 48 formed between the top surface 44 and bottom surface 46. Sensor region 48 may be accessible through a circular aperture 50 in bottom surface 46 and may be configured to receive the neck portion 52 and cap 54 of bottle 42 when it is inserted into the sensor region 48, until the cap 54 contacts the stop surface 56, thereby preventing further insertion of bottle 42 into the sensor region 48. In this position the outer diameter of aperture 50 rests on the shoulder 57 of bottle 42.

Sensor unit 40 may also include a sidewall 58 which extends from the first end 44 toward the second end 46. The side wall may comprise four discrete side walls 58a-d, if sensor unit 40 is in the shape of a cube, as is shown in FIGS. 2 and 3. Sensor unit 40 may also be in the shape of a cylinder, in which case sidewall 58 may be formed as one continuous surface. Sensor unit 40 may take on various shapes as long as it meets a certain required design feature; namely, that when it is placed on the container, it receives the container in the sensor region such that the bottle is positioned a desired distance, d, from stop surface 50, as shown in FIG. 1 at line 27 and as will be described below. The desired distance d corresponds to the position along the height of the bottle having a known diameter or path length, l, across the cross-section of the bottle.

Within the sidewall 58 of sensor unit 40 is affixed an infrared emitter 60 configured to transmit NIR radiation across the sensor region 48 to an infrared detector or spectrometer 62, also affixed to the sidewall 58, positioned opposite infrared transmitter 60. Infrared transmitter 60 and infrared detector 62 are positioned such that the NIR radiation is transmitted over a transmission path 64, aligned with the desired position along the length of the bottle having the desired path length, l. Thus, the infrared transmitter 60 and infrared detector 62 are also located distance, d, from the stop surface 56 and the top of cap 54 of bottle 42. A temperature sensor 66 is also included to measure the temperature within sensor region 48. Gas concentration measurements in the liquid are dependent on temperature, so the reading of temperature sensor is used to determine gas concentration in the liquid from the determined gas concentration in the headspace, as described below.

Infrared transmitter 60 and infrared detector 62, along with the temperature sensor 68, are in communication with data processing module 70 via cable, which may be connected to sensor unit 40 via jack 72 and connected to data processing module 70 via jack 74. Instead of a hard wired connection, sensor unit 40 may be connected to processing module 70 via a wireless connection. Alternatively, processing module 70 may be integrated into the sensor unit 40.

The combination of sensor unit 40 and data processing module 70 form the non-destructive gas concentration analyzer 30, according to this invention. The computing device 70 may take various forms, including a laptop computer, a tablet, smartphone or a dedicated handheld device. Processing module 70 may control the transmission and reception of NIR energy as activated by a user via a user interface on a display 76, as well as the calculations required to determine gaseous species concentrations in bottle 42. The gaseous species concentration may be displayed on the display 76 for the user to read.

Figure 4:
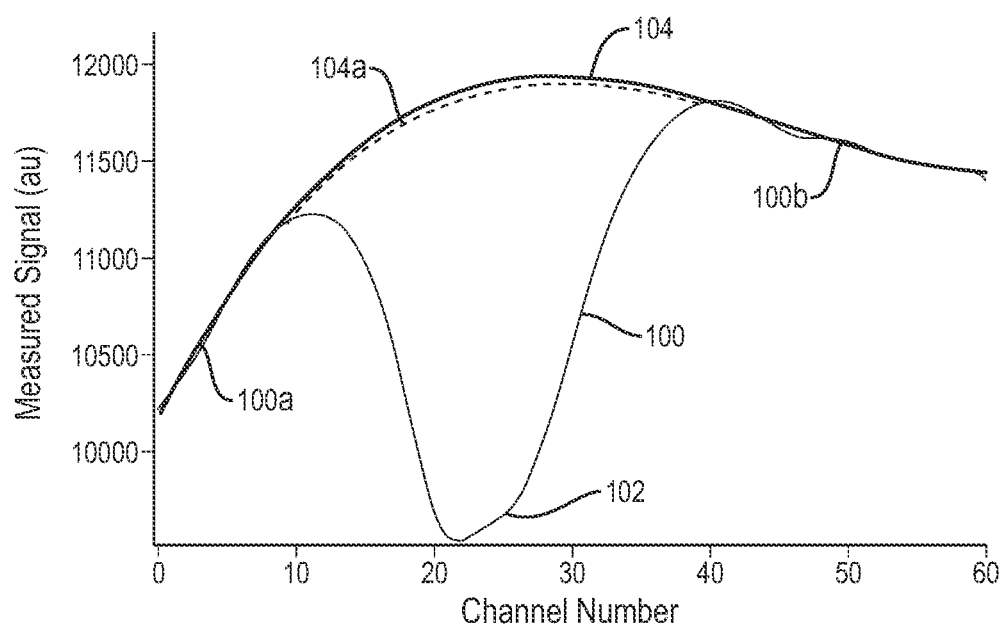
FIG. 4 is a spectrum waveform output of the sensor unit of FIG. 2A after having passed through a sealed carbonated beverage container.

Infrared transmitter 60 may output NIR energy across a wavelength range of 750 to 2,500 nm (wavenumbers: 13,300 to 4,000 $cm^{-1}$) or a subset of this range. The output signal from infrared detector 62 represents the amount of the transmitted NIR energy received after it passes through a sealed carbonated beverage container. An example of the output of infrared detector after having passed through a sealed carbonated beverage container is depicted by spectrum waveform 100, FIG. 4. There is a clear drop-out or reduction of received energy as indicated at trough 102, which is proximate the 2000 nm wavelength. This corresponds to the wavelength at which carbon dioxide absorbs NIR energy and can be used to determine carbon dioxide concentration. However, in order to accurately calculate the concentration of carbon dioxide in the bottle, a baseline spectrum representing the received NIR spectrum when there is no carbon dioxide in the bottle must be established. By comparing the baseline spectrum to the detected spectrum, any artifacts in the detected spectrum caused by the bottle material itself or the transmitter/detector may be normalized because the baseline spectrum also incorporates those same artifacts and rules them out, thereby leaving a curve which is impacted only by the effects of carbon dioxide in the bottle.

For a given bottle type, a baseline spectrum may be measured in advance and stored within processing module 70. This, however, is cumbersome and requires that the system be preloaded with baseline measurements for all possible bottle types to be measured. According to an aspect of this invention, an interpolated baseline spectrum may be derived from the detected spectrum. With this approach the computing device does not need to be preloaded with measured baseline spectrums for the various carbonated bottles to be detected. Instead, the interpolated baseline spectrum may be obtained each time a concentration measurement is made and it may be done by using only the detected spectrum.

Referring again to FIG. 4, there is shown a baseline spectrum 104, which was measured in advance on a bottle containing no carbon dioxide. The measured baseline spectrum is only included here for illustration purposes and does not need to be utilized with this invention. In addition, there is shown an interpolated baseline spectrum 104a obtained according to an aspect of this invention. This may be accomplished by utilizing portions of detected spectrum 100 outside the wavelengths at which carbon dioxide absorbs NIR energy, e.g. on either side of the trough 102. Trough 102 begins to dip downward at about 1000 nm and returns to track with the baseline spectrum 104 at about 4000 nm. Therefore, region 100a (below 1000 nm) and region 100b (above 4000 nm) on either side of peak 102, may be utilized. By using data points on either side of trough 102, in regions 100a and 100b, a non-linear curve fit calculation may be made to interpolate the data points between the regions 100a and 100b and thus form an interpolated baseline spectrum 104a. It can be seen in FIG. 4 that the actual measured baseline spectrum 104 is quite comparable to the interpolated baseline spectrum 104a.

The interpolated baseline spectrum is obtained by performing a nonlinear curve fitting to the actual detected spectrum by excluding that portion of the spectrum where carbon dioxide absorption occurs in the NIR, i.e. across the trough 102. The interpolated spectrum is a mathematical reconstruction of the absorption spectrum without carbon dioxide, i.e., exclusively due to bottle container material. The non-linear curve fitting may be carried out using a higher order polynomial curve fitting approach, a spline curve fitting approach, or another suitable approach.

Figure 5:
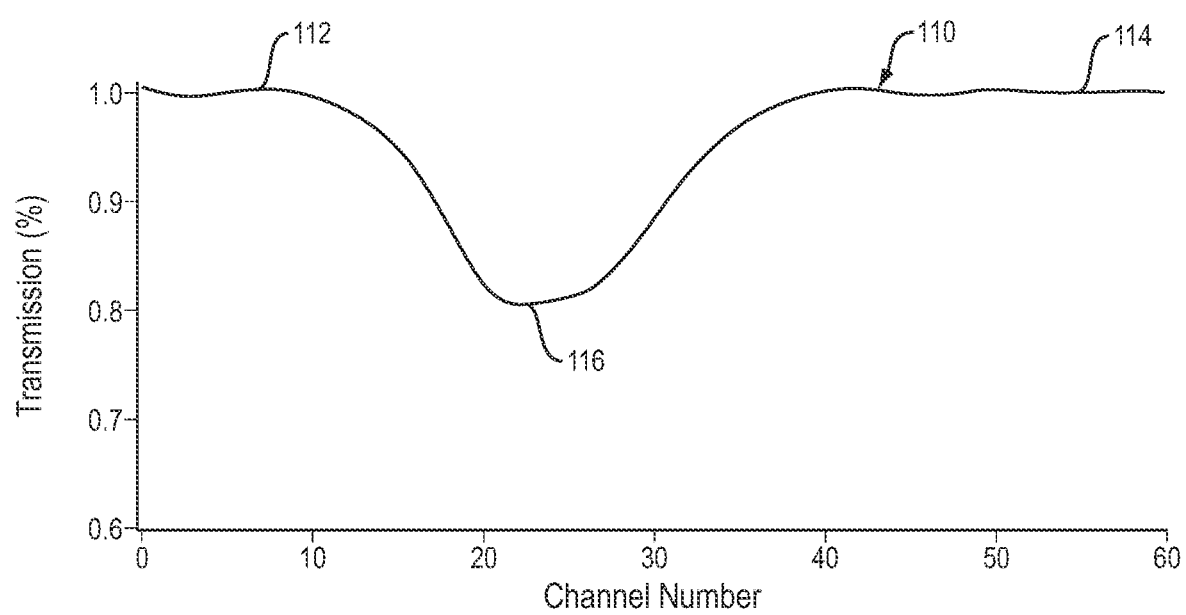
FIG. 5 is a normalized version of the spectrum waveform depicted in FIG. 4 processed according to an aspect of the invention.

The interpolated baseline spectrum 104a may be used to normalize the detected spectrum 100 by dividing detected spectrum 100 by the interpolated baseline spectrum 104a to arrive at a normalized spectrum 110, FIG. 5. As used herein, "normalized" refers to measurement of the carbon dioxide by ruling out any influence of the container material on the measurement. Consequently, any decrease in energy transmission is exclusively due to carbon dioxide.

Normalized spectrum 110 depicts the percentage of energy transmitted by infrared transmitter 60 that was received by infrared detector 62 across the wavelength spectrum. In regions 112 and 114, between the trough 116, the detected energy is at 100% versus the detected energy at peak 116, which is approximately 80% of the transmitted energy. Thus, the amount of carbon dioxide in this example, caused 20% of the transmitted NIR energy to be absorbed.

Referring to Equation (1) above, the absorbance of energy, A, due to the presence of carbon dioxide in the bottle may be determined. With the normalized spectrum 110 representing the transmitted energy, T, absorbance, A, may be found according to the following equation:

$$A = -\log 1/T \quad \text{Equation (2)}$$

With the absorbance of energy, A, calculated according to equation (2), the path length, l, known, and the molar absorption coefficient, ε, being a fixed value, using Equation (1) above, the concentration, c, of carbon dioxide in the headspace of the bottle may be determined as follows:

$$Cgas = A/\varepsilon l \quad \text{Equation (3)}$$

From the concentration of gas in the headspace, as determined by equation (3), the gas concentration dissolved in the liquid, Cliq, may be calculated using the following formula:

$$Cgas = Cliq * H(T) \quad \text{Equation (4)}$$

The gas concentration of the liquid, Cliq, from the gas concentration in the headspace, Cgas, may be determined by using Henry's law, H(T). Henry's law is a function of temperature. It is know that at lower temperatures, more of the total amount of gas in a container will be dissolved in liquid and less will be contained in the headspace. Conversely, at higher temperatures, more of the total gas will be in the headspace and less of the gas will be dissolved in the liquid.

By simultaneously measuring the temperature and the headspace gaseous concentration, Cgas, as is done by the sensor unit 40, described above, Henry's law can yield the gaseous concentration inside the liquid, Cliq, in the container.

$$H(T) = H0 * \exp^{[-DH/R*(1/T - 1/T0)]} \quad \text{Equation (5)}$$

In this equation, DH is the enthalpy change, R is the gas constant for the particular gaseous species being detected, T0 is a reference temperature, T is the temperature detected by temperature sensor 66, and H0 is the Henry's Law constant at the reference temperature T0. Using equations (4) and (5), a look-up table may be created and stored in memory with values for various gas concentrations, Cgas, and corresponding gas concentration of the liquid, Cliq, for a range of possible temperatures. Using the calculated gas concentration and measured temperature (as described above), the look-up table may be used to find the corresponding gas concentration in the liquid. Here is an example of a portion of a look-up table for carbon dioxide concentrations at various temperatures:

| Cgas, atm | Cliq, gram/liter | Temperature, celsius |
|---|---|---|
| 1.8 | 5.0 | 0 |
| 2.4 | 5.0 | 10 |
| 2.8 | 5.0 | 15 |
| 3.2 | 5.0 | 20 |

As an example, for a calculated gas concentration of 1.8 atm in the headspace of the bottle at a temperature of 0, the gas concentration in the liquid of 5.0 g/l may be retrieved from the look-up table and output on the display as the measured gas concentration in the liquid.

Non-Limiting Computing Device Examples

Figure 6:
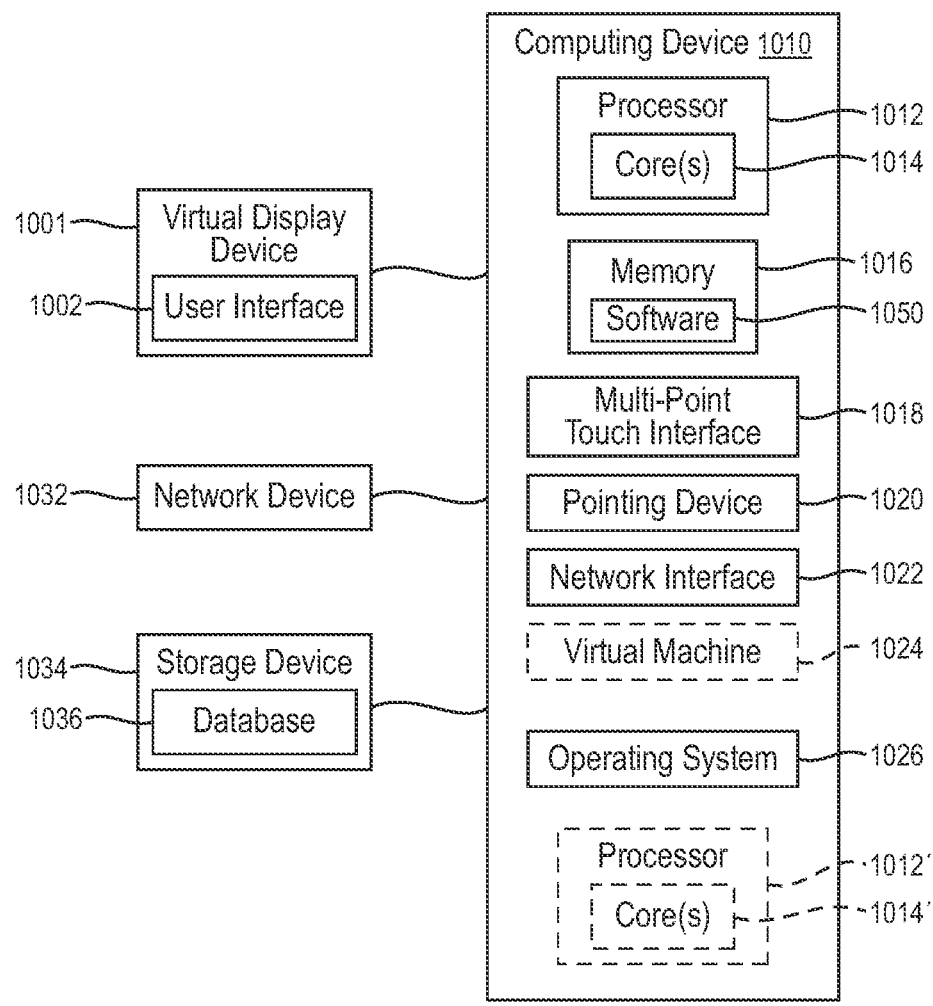
FIG. 6 is a block diagram of an exemplary computing system for the gas analyzer according to the invention.

FIG. 6 is a block diagram of an exemplary computing device 1010 such as may be used, or portions thereof, e.g. processing module 70, in accordance with various embodiments as described above with reference to FIGS. 1-5. The computing device 1010 includes one or more non-transitory computer-readable media for storing one or more computer-executable instructions or software for implementing exemplary embodiments. The non-transitory computer-readable media may include, but are not limited to, one or more types of hardware memory, non-transitory tangible media (for example, one or more magnetic storage disks, one or more optical disks, one or more flash drives), and the like. For example, memory 1016 included in the computing device 1010 may store computer-readable and computer-executable instructions or software for performing the operations disclosed herein. For example, the memory may store software application 1040 which is programmed to perform various of the disclosed operations as discussed with respect to FIGS. 1-5. The computing device 1010 may also include configurable and/or programmable processor 1012 and associated core 1014, and optionally, one or more additional configurable and/or programmable processing devices, e.g., processor(s) 1012' and associated core (s) 1014' (for example, in the case of computational devices having multiple processors/cores), for executing computer-readable and computer-executable instructions or software stored in the memory 1016 and other programs for controlling system hardware. Processor 1012 and processor(s) 1012' may each be a single core processor or multiple core (1014 and 1014') processor.

Virtualization may be employed in the computing device 1010 so that infrastructure and resources in the computing device may be shared dynamically. A virtual machine 1024 may be provided to handle a process running on multiple processors so that the process appears to be using only one computing resource rather than multiple computing resources. Multiple virtual machines may also be used with one processor.

Memory 1016 may include a computational device memory or random access memory, such as but not limited to DRAM, SRAM, EDO RAM, and the like. Memory 1016 may include other types of memory as well, or combinations thereof.

A user may interact with the computing device 1010 through a visual display device 1001, 111A-D, such as a computer monitor, which may display one or more user interfaces 1002 that may be provided in accordance with exemplary embodiments. The computing device 1010 may include other I/O devices for receiving input from a user, for example, a keyboard or any suitable multi-point touch interface 1018, a pointing device 1020 (e.g., a mouse). The keyboard 1018 and the pointing device 1020 may be coupled to the visual display device 1001. The computing device 1010 may include other suitable conventional I/O peripherals.

The computing device 1010 may also include one or more storage devices 1034, such as but not limited to a hard-drive, CD-ROM, or other computer readable media, for storing data and computer-readable instructions and/or software that perform operations disclosed herein. Exemplary storage device 1034 may also store one or more databases for storing any suitable information required to implement exemplary embodiments. The databases may be updated manually or automatically at any suitable time to add, delete, and/or update one or more items in the databases.

The computing device 1010 may include a network interface 1022 configured to interface via one or more network devices 1032 with one or more networks, for example, Local Area Network (LAN), Wide Area Network (WAN) or the Internet through a variety of connections including, but not limited to, standard telephone lines, LAN or WAN links (for example, 802.11, T1, T3, 56 kb, X.25), broadband connections (for example, ISDN, Frame Relay, ATM), wireless connections, controller area network (CAN), or some combination of any or all of the above. The network interface 1022 may include a built-in network adapter, network interface card, PCMCIA network card, card bus network adapter, wireless network adapter, USB network adapter, modem or any other device suitable for interfacing the computing device 1010 to any type of network capable of communication and performing the operations described herein. Moreover, the computing device 1010 may be any computational device, such as a workstation, desktop computer, server, laptop, handheld computer, tablet computer, or other form of computing or telecommunications device that is capable of communication and that has sufficient processor power and memory capacity to perform the operations described herein.

The computing device 1010 may run any operating system 1026, such as any of the versions of the Microsoft® Windows® operating systems (Microsoft, Redmond, Wash.), the different releases of the Unix and Linux operating systems, any version of the MAC OS® (Apple, Inc., Cupertino, Calif.) operating system for Macintosh computers, any embedded operating system, any real-time operating system, any open source operating system, any proprietary operating system, or any other operating system capable of running on the computing device and performing the operations described herein. In exemplary embodiments, the operating system 1026 may be run in native mode or emulated mode. In an exemplary embodiment, the operating system 1026 may be run on one or more cloud machine instances.

While the foregoing description of the invention enables one of ordinary skill to make and use what is considered presently to be the best mode thereof, those of ordinary skill will understand and appreciate the existence of variations, combinations, and equivalents of the specific embodiments and examples herein. The above-described embodiments of the present invention are intended to be examples only. Alterations, modifications and variations may be effected to the particular embodiments by those of skill in the art without departing from the scope of the invention, which is defined solely by the claims appended hereto. The invention is therefore not limited by the above described embodiments and examples.

We claim:

1. A gas analyzer to non-destructively determine the concentration of a gas in a pressurized transparent or semi-transparent container having a neck portion extending from a shoulder and terminating in an opening, the opening being sealed with a cap, comprising:
    a sensor unit including:
        a first surface, a second surface, opposite the first surface, and a sensor region between the first and second surfaces, the sensor region including a first end having a stop surface and the second end including an aperture, in communication with the sensor region, configured to receive a neck portion of a container in the sensor region until a cap contacts the stop surface; the sensor unit further includes at least one sidewall extending from the first surface toward the second surface;
        an infrared emitter affixed to the at least one sidewall and configured to transmit infrared radiation across the sensor region; and
        an infrared detector affixed to the at least one sidewall, opposite the infrared emitter, and configured to receive infrared radiation transmitted by the infrared emitter across the sensor region and to provide an output signal corresponding to the received infrared radiation;
        wherein the infrared emitter and the infrared detector are each affixed to the at least one sidewall, spaced a distance, d, from the stop surface in the direction of the aperture, wherein the distance, d, corresponds to a predetermined distance from the cap to a location on the neck portion of the container; and
    a processor module, in communication with the sensor unit, configured to receive the output signal from the infrared detector and to determine a concentration of the gas in the container.

2. The gas analyzer of claim 1 wherein the infrared radiation comprises near infrared radiation.

3. The gas analyzer of claim 1 wherein the sensor unit includes four sidewalls, and wherein the infrared transmitted is affixed to a first sidewall and the infrared detector is affixed to a second sidewall opposite the first sidewall.

4. The gas analyzer of claim 1 wherein spacing the infrared transmitter and the infrared detector the distance, d, from the stop surface in the direction of the aperture, which corresponds to a predetermined distance from the cap to a location on the neck portion of the container, provides a fixed transmission path length across the neck portion of the container.

5. The gas analyzer of claim 1 wherein the processor module is separate from the sensor unit.

6. The gas analyzer of claim 1 wherein the processor module includes a display device configured to display the concentration of the gas determined to be in the container.

7. The gas analyzer of claim 1 wherein the container is partially filled with a liquid and the interior region of the container above the liquid constitutes a headspace, and wherein the distance d from the cap to a location on the neck portion of the container is positioned within the headspace.

8. The gas analyzer of claim 7 further including a temperature sensor in communication with the sensor region and wherein the processor module uses the output signal to determine a gas concentration in the headspace, and from the gas concentration in the head space and a temperature measured in the sensor region by the temperature sensor, the processor module determines a gas concentration in the liquid.

9. A gas analyzer to non-destructively detect the concentration of a gas in a pressurized transparent or semi-transparent container, comprising:
   a sensor unit including;
      an infrared emitter configured to be positioned on a first side of a pressurized container and to transmit infrared radiation over a path through the pressurized container; wherein the infrared radiation has an infrared spectrum including wavelengths which absorb a gas in the pressurized container and wavelengths which do not absorb the gas in the pressurized container;
      an infrared detector configured to be positioned on a second side of the pressurized container, opposite the first side, and configured to receive a portion of the infrared radiation transmitted by the infrared emitter over the path through the pressurized container and to produce detected spectrum corresponding to the received radiation; and
   a processor module, in communication with the sensor unit, configured to:
      receive the detected spectrum from infrared detector, the detected spectrum including a trough region at wavelengths which absorb the gas in the pressurized container;
      form an interpolated baseline spectrum from the detected spectrum by interpolating baseline data points spanning the trough region; and
      calculate a gas concentration in the pressurized container using the detected spectrum and the interpolated baseline spectrum.

10. The gas analyzer of claim 9 wherein the infrared radiation comprises near infrared radiation.

11. The gas analyzer of claim 9 wherein the sensor unit includes a first surface, a second surface, opposite the first surface, and a sensor region between the first and second surfaces, the sensor region within the sensor unit including a first end having a stop surface and the second end including an aperture, in communication with the sensor region, and configured to receive a neck portion of a container in the sensor region until a cap contacts the stop surface; the sensor unit further includes at least one sidewall extending from the first surface toward the second surface.

12. The gas analyzer of claim 11 wherein the infrared emitter and the infrared detector are each affixed to the at least one sidewall, spaced a distance, d, from the stop surface in the direction of the aperture, wherein the distance, d, corresponds to a predetermined distance from the cap to a location on the neck portion of the container.

13. The gas analyzer of claim 12 wherein spacing the infrared transmitter and the infrared detector the distance, d, from the stop surface in the direction of the aperture, which corresponds to a predetermined distance from the cap to a location on the neck portion of the container, provides a fixed transmission path length across the neck portion of the container.

14. The gas analyzer of claim 13 wherein the container is partially filled with a liquid and the interior region of the container above the liquid constitutes a headspace, and wherein the distance d from the cap to a location on the neck portion of the container is positioned within the headspace.

15. The gas analyzer of claim 14 further including a temperature sensor in communication with the sensor region and wherein the processor module uses the output signal to determine a gas concentration in the headspace, and from the gas concentration in the head space and a temperature measured in the sensor region by the temperature sensor, the processor module determines a gas concentration in the liquid.

16. The gas analyzer of claim 15 wherein the processor module is further configured to use a plurality of data points on each side of the trough to perform a non-linear curve fitting to obtain the baseline data points spanning the trough region.

17. The gas analyzer of claim 16 wherein the processor module is further configured to divide the detected spectrum by the interpolated baseline spectrum to produce a normalized spectrum indicative of the energy received by infrared detector.

18. The gas analyzer of claim 17 wherein the processor module is further configured to determine an absorbance of energy due to the gas using the normalized spectrum.

19. The gas analyzer of claim 18 wherein the processor module is further configured to, using the absorbance of energy, calculate a concentration of the gas in the headspace of the container.

20. The gas analyzer of claim 19 wherein the processor module is further configured to, using the concentration of the gas in the headspace and the temperature in the sensor region, determine a concentration of the gas dissolved in the liquid.

21. The gas analyzer of claim 9 wherein the sensor unit includes four sidewalls, and wherein the infrared transmitted is affixed to a first sidewall and the infrared detector is affixed to a second sidewall opposite the first sidewall.

22. The gas analyzer of claim 9 wherein the processor module is separate from the sensor unit.

23. The gas analyzer of claim 9 wherein the processor module includes a display device configured to display the concentration of the gas determined to be in the container.

24. A method to non-destructively detect the concentration of a gas in a pressurized transparent or semi-transparent container, the method comprising:

transmitting, using an infrared emitter positioned on a first side of a pressurized container, infrared radiation over a path through the pressurized container; wherein the infrared radiation has an infrared spectrum including wavelengths which absorb a gas in the pressurized container and wavelengths which do not absorb the gas in the pressurized container;

receiving, using an infrared detector positioned on a second side of the pressurized container, opposite the first side, a portion of the infrared radiation transmitted by the infrared emitter over the path through the pressurized container and to produce detected spectrum corresponding to the received radiation;

receiving the detected spectrum from infrared detector, the detected spectrum including a trough region at wavelengths which absorb the gas in the pressurized container;

forming an interpolated baseline spectrum from the detected spectrum by interpolating baseline data points spanning the trough region; and calculating a gas concentration in the pressurized container using the detected spectrum and the interpolated baseline spectrum.

25. The method of claim 24 wherein the infrared radiation comprises near infrared radiation.

26. The method of claim 24 wherein the infrared transmitter and the infrared detector are spaced a predetermined distance from a cap of the container to a location on the neck portion of the container to provide a fixed transmission path length across the neck portion of the container.

27. The method of claim 26 wherein the container is partially filled with a liquid and the interior region of the container above the liquid constitutes a headspace, and wherein the fixed transmission path length is positioned within the headspace.

28. The method of claim 27 further including determining a temperature proximate the container, using the detected spectrum to determine a gas concentration in the headspace, and, from the gas concentration in the head space and temperature proximate the container, determining a gas concentration in the liquid.

29. The method of claim 28 further including using a plurality of data points on each side of the trough to perform a non-linear curve fitting to obtain the baseline data points spanning the trough region.

30. The method of claim 29 further including dividing the detected spectrum by the interpolated baseline spectrum to produce a normalized spectrum indicative of the energy received by infrared detector.

31. The method of claim 30 further including determining an absorbance of energy due to the gas using the normalized spectrum.

32. The method of claim 31 further including, using the absorbance of energy, calculating a concentration of the gas in the headspace of the container.

33. The method of claim 32 further including, using the concentration of the gas in the headspace and the temperature in the sensor region, determining a concentration of the gas dissolved in the liquid.

34. The method of claim 24 including displaying the concentration of the gas determined to be in the container.

* * * * *